(12) United States Patent
Coster et al.

(10) Patent No.: US 8,947,104 B2
(45) Date of Patent: Feb. 3, 2015

(54) IN SITU MEMBRANE MONITORING

(71) Applicant: Inphaze Pty Ltd, Mosman (AU)

(72) Inventors: Hans Gerard Leonard Coster, Randwick (AU); Terry Calvin Chilcott, Sans Souci (AU)

(73) Assignee: Inphaze Pty Ltd, Mosman, New South Wales ( * ) Notice: Subject to any disclaimer, the term of this patent is extended or adjusted under 35 U.S.C. 154(b) by 0 days.

(21) Appl. No.: 14/082,490

(22) Filed: Nov. 18, 2013

(65) Prior Publication Data
US 2014/0076030 A1    Mar. 20, 2014

Related U.S. Application Data

(62) Division of application No. 12/677,890, filed as application No. PCT/AU2008/001356 on Sep. 11, 2008, now Pat. No. 8,610,440.

(30) Foreign Application Priority Data

Sep. 14, 2007    (AU) ................ 2007905045

(51) Int. Cl.
*G01R 27/26*    (2006.01)
*G01N 27/12*    (2006.01)
(Continued)

(52) U.S. Cl.
CPC ............ *G01N 27/12* (2013.01); *B01D 61/025* (2013.01); *B01D 61/12* (2013.01); *B01D 63/103* (2013.01); *B01D 65/104* (2013.01); *G01N 27/02* (2013.01); *G01N 7/10* (2013.01); *B01D 2313/345* (2013.01)
USPC ........................................ 324/654

(58) Field of Classification Search
CPC ................ G01N 33/5438; G01N 2015/129; G01N 2021/775; C08J 5/22; B01D 63/103; B01D 61/025
See application file for complete search history.

(56) References Cited

U.S. PATENT DOCUMENTS

| | | |
|---|---|---|
| 5,096,584 A | 3/1992 | Reddy et al. |
| 6,161,435 A | 12/2000 | Bond et al. |

(Continued)

FOREIGN PATENT DOCUMENTS

WO    2007143786    12/2007

OTHER PUBLICATIONS

Written Opinion of the International Searching Authority; 9 pages; Australian Patent Office; Dec. 10, 2008.

(Continued)

*Primary Examiner* — Tung X Nguyen
(74) *Attorney, Agent, or Firm* — Thomas | Horstemeyer, LLP

(57) ABSTRACT

A method for in situ monitoring of a membrane of a membrane separation system comprises measuring a complex impedance of the membrane at a plurality of frequencies to provide an indication of the electrical conduction and electrical polarization properties of the membrane. The membrane based separation system for removing or reducing the concentration of materials carried in a fluid including a separation membrane has a first pair of electrodes separated by the membrane and arranged for measurement of the complex impedance of the membrane at a plurality of frequencies to provide the indication of the membrane properties. There may also be a second pair of electrodes separated by the membrane for injecting the stimulus current such that the injecting and monitoring functions are separated.

17 Claims, 8 Drawing Sheets

(51) Int. Cl.
*B01D 61/02* (2006.01)
*B01D 61/12* (2006.01)
*B01D 63/10* (2006.01)
*B01D 65/10* (2006.01)
*G01N 27/02* (2006.01)
*G01N 7/10* (2006.01)

(56) References Cited

U.S. PATENT DOCUMENTS

| | | |
|---|---|---|
| 6,169,394 B1 | 1/2001 | Frazier et al. |
| 6,607,647 B2 | 8/2003 | Wilkins et al. |
| 6,727,099 B2 | 4/2004 | Chun et al. |
| 6,838,001 B2 | 1/2005 | Zeiher et al. |
| 7,563,614 B2 * | 7/2009 | Orwar et al. ............ 435/286.2 |
| 8,759,017 B2 * | 6/2014 | Owen et al. ............ 435/7.2 |
| 2004/0266017 A1 | 12/2004 | Chun et al. |
| 2005/0211638 A1 | 9/2005 | Schrive et al. |

OTHER PUBLICATIONS

Electrophoresis in Membrane Separation Processes: From Lab to Field Scale Experiments; G. Falk; Department of Powder Technology, Saarland University, 66123 Saarbruecken, Germany; 1 page.

* cited by examiner

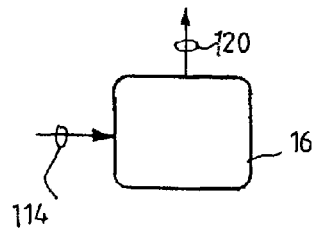
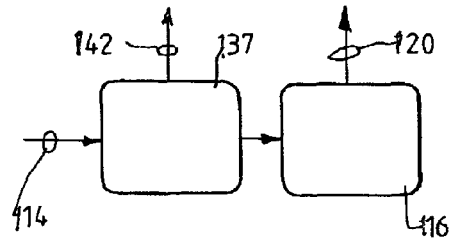
FIGURE 10          FIGURE 11
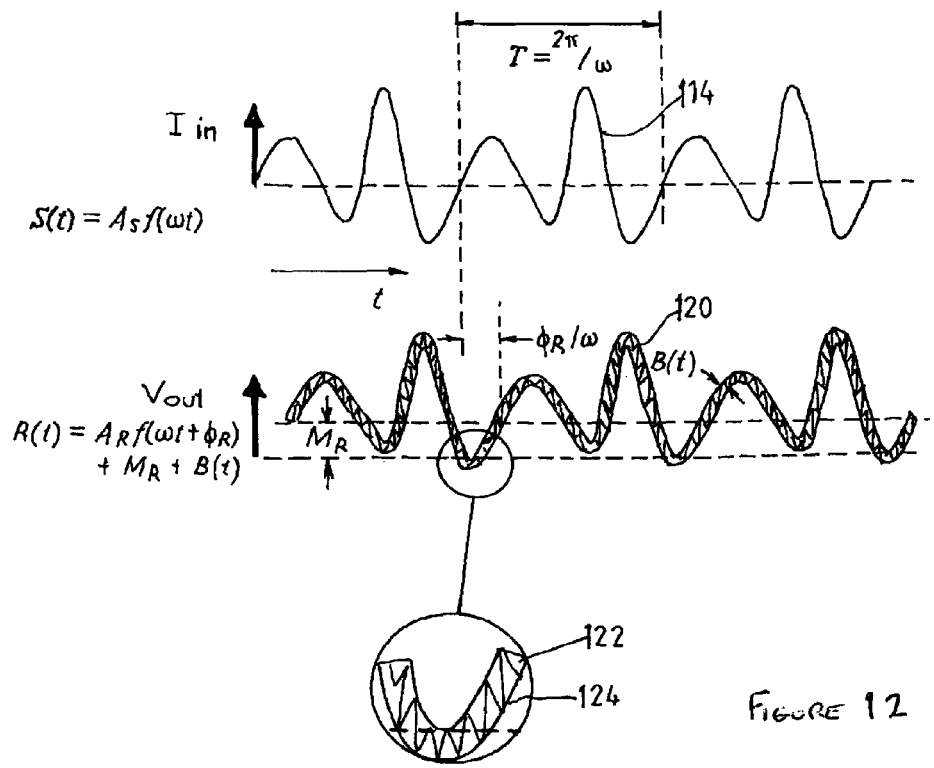
FIGURE 12

IN SITU MEMBRANE MONITORING

CROSS-REFERENCE TO RELATED APPLICATIONS

This application is a divisional of a U.S. Patent Application entitled "In Situ Membrane Monitoring", assigned Ser. No. 12/677,890, filed Mar. 12, 2010 now U.S. Pat. No. 8,610,440, which claimed priority to PCT Application No. PCT/AU08/001356, international filing date 11 Sep. 2008, which claimed priority to Australian Application No. 2007905045, filed on 14 Sep. 2007.

FIELD OF THE INVENTION

This invention relates to a device and method for making impedance spectroscopy measurements of membranes in membrane separation modules

BACKGROUND OF THE INVENTION

Membrane separation systems are used for a wide variety of processes in which it is desired to remove or reduce the concentration of certain materials in a fluid. In particular they are used to purify waste water effluents from industrial and domestic water use. They are also increasingly being used for producing fresh water from sea water or brackish water supplies by removing the salt, and other contaminants, from saline feed water.

The performance of membrane separation systems depends on many operational parameters such as the:
   pressure of the feed fluid,
   pressure of the permeate fluid (or flux),
   pressure of the discard (or sludge),
   cross flow velocity, the concentration,
   the nature of the materials to be removed,
   temperature etc.

The performance is also dependent on the intrinsic properties of the membrane material.

The overall operational capacity of a membrane increases with surface area. The size of the modules incorporating the membranes also increases with the area of the membranes. In one of the most common physical configurations the ratio of the membrane area to the volume of the module is minimized by wrapping the membranes in a spiral around a central permeate collection tube. In these so called "Spiral Wound" modules the membrane surfaces are kept apart by a spacer fabric which is usually made of polymer strands.

During operation, the surfaces of the membrane become covered with materials present in the feed solution to which the membrane is highly impermeable. The flux or fluid permeating through the membrane is then largely devoid of such materials. The materials rejected by the membrane are swept along by the cross flow and appear in the discarded fluid (also referred to as the sludge).

Under some circumstances, and after prolonged use of the system, some of the materials that are present in the sludge at high concentrations become attached to the membrane and in some circumstances become permanently attached to the surface. This is known as "Fouling". Fouling leads to a reduced permeate flux and can also lead to a decrease in the rejection characteristics of the membrane. Any reduction in the rejection characteristics has a significant negative impact, particularly on the performance of so called "Reverse Osmosis" membranes for removing salt from sea water or brackish feed water.

In particular, fouling in such membranes will give rise to reduced salt rejection and hence lower quality (higher salinity) permeate fluxes. Many factors contribute to the fouling process, including dynamic effects arising from concentration polarization layers at the membrane surface. From an operational point of view it is important to monitor the performance of the system and to take remedial steps to remove fouling of the membranes. The studies of Li et al (Journal of Membrane Science. 149 pp. 83-97, 1998), Kwon, Vigneswaran, Fane and Ben Aim R., in Separation and Purification. Technology, 19 pp. 169-181(2000) and Zhang et al (Journal of Membrane Science. 282; 189-197, 2006) teach that the rate of fouling dramatically increases when a system is operated so that the permeate flux exceeds certain critical values.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

In a first broad aspect the present invention provides a method for in situ monitoring of changes in a membrane of a membrane separation system and the formation of external films and layers on the membrane during separation processes.

More specifically, in a particular aspect the present invention provides a method of monitoring a membrane or membranes of a membrane based separation device wherein the impedance magnitude and phase of the membranes are measured at a plurality of frequencies to provide an indication of the electrical conduction and electrical polarization properties of the membrane.

In one embodiment, the measurements are made using electrodes located close to or attached to the membranes.

In a related aspect the present invention provides a membrane based separation device for removing or reducing the concentration of materials carried in a fluid including at least one separation membrane and at least one pair of electrodes arranged for measurement of the impedance magnitude and phase of the membranes are measured at a plurality of frequencies to provide a indication of the electrical conduction and electrical polarization properties of the membrane.

In order to make impedance measurements, small alternating electric currents are passed through the membrane or a patch of the membrane (referred to hereinafter as the stimulus) and the electrical potential developed across the membrane (referred to hereinafter as the response) as well as the phase difference between the stimulus and response signals are measured. To achieve that in the present invention, electrodes are fitted inside the membrane module.

Severe fouling of the membranes will give rise to reduced permeate fluxes for a given set of operating parameters. Fouling of the membranes will result in changes to the magnitude and relative phase of the impedance of the membranes, dependant on frequency. By measuring the impedance of the membranes, the present invention enables early and continuous detection of the onset of fouling and the formation of foulant layers on the membrane to allow remedial action to be taken. Remedial action may include alteration of the operational pressures and flow velocities and ultimately specific cleaning regimes for restoring membrane performance.

In one preferred embodiment of the present invention, the spiral wound membrane module is fitted with electrodes located within the spacer fabric on the two opposite sides of the membrane. The two electrodes on either side of a membrane in the module are used for injecting the stimulus signal and a further set of two electrodes are used to measure the response signal developed across the membrane. One suitable "four terminal method" of electrical impedance measurements is taught in International Patent Application No PCT/AU2007/000830 by Coster and Chilcott entitled "A System for complex impedance measurement", the contents of which are incorporated herein by reference.

One advantage of using such a four-terminal method is that fouling of the electrodes themselves will not affect the measurement of the membrane impedance to any significant degree. Another advantage is that use of four-terminal measurement eliminates the impedance of the electrode-solution interface from the total impedance measured.

In another alternative embodiment, two electrodes only are embedded in the spacer fabric, one on each side of the membrane. The impedance measurements can then be made using the same pair of electrodes to inject the stimulus signal and to measure the response. Generally speaking, this method would have the relative disadvantage of potentially being more subject to interference from fouling and other factors, but it may be simpler and cheaper to manufacture the device.

The placement of the electrodes within the module can be designed to enable monitoring of the various parts of the membranes within the module such as the feed side, discharge end and so on, or the module may be fitted with multiple sets of electrodes to monitor the membrane at a variety of locations within the module.

In one preferred embodiment, the spacer fabric itself could be constructed out of an electrically conducting material, such as stainless steel mesh, and the spacers themselves could then be used as the electrodes for the impedance measurements.

In a preferred embodiment, an electrode is placed on each side of a membrane. This involves electrodes being embedded in the spacer on both the permeate side and feed side of the membrane.

In an alternative embodiment, it is possible to place the electrodes such that the stimulus signal is applied to two membranes in series. This involves placing the electrodes in either two feed side channels separated by two membranes and a permeate channel or placing the electrode pairs in two permeate side channels separated by two membranes and a feed side channel. This configuration can be used with a four-terminal measurement, using four electrodes or a two-terminal measurement using two electrodes. There may be some advantage in making measurements in which both electrodes in the case of two-terminal measurements, or two pairs of electrodes in the case of four-terminal measurements, are present in the same solution, that is either in the feed solution or the permeate solution. This is because when such electrodes are in different solutions the electrochemical processes at the electrode-solution interfaces may create electric potential that produced voltage offsets. Whilst such voltage offsets can be allowed for in making the measurements they may, under severe circumstances, reduce the precision that can be obtained in making the impedance magnitude and phase determinations.

It is preferred that the electrodes imbedded in the membrane of the module are electrically connected to electrode terminals on the outside of a pressure vessel that encompasses the membrane module so that the impedance measurements can be conducted without interrupting the operation of the module.

The impedance measurements facilitated by the electrodes placed in the membrane module, as described above, may also be used to monitor the electrical conductivity of the feed solution and or the permeate solution. Such information for the permeate fluid can provide an indication of loss of membrane integrity or important changes in the operational parameters such as a decrease in, for instance, the salt rejection. Changes in the electrical conductivity of the feed solution may indicate important changes in the operational parameters that might require intervention. The configurations of electrodes described above where the electrodes or pairs of electrodes are separated by two membranes in series, would be particularly suited to making such measurements, although the other configurations would also allow the fluid conductivities to be deduced from the data.

The electrodes incorporated in the membrane module should be constructed from a material that is a conductor of electricity. Preferentially the electrodes and the electrode leads that are accessible from the outside of the module should be constructed out of the same material to avoid complications that may arise from electrochemical reactions between different components when they are immersed in the fluids.

The leads connecting the electrodes to the outside of the module should preferentially be covered or coated with an electrically insulating material so that only the electrodes themselves are exposed.

The electrodes used to inject the stimulus currents and or the electrodes used to measure the response to the stimulus could extend over the entire length of the membrane module. Measurements made using such electrode configurations would yield information about the overall state of the membranes. If the electrodes are used to also monitor the conductivities of the feed or permeate solutions then such an electrode configuration would also provide information of the overall performance.

Configurations of membrane modules other than a spiral wound membrane are possible. One such configuration is a "Flat bed membrane module". The placement of electrodes on two sides of the membrane, using the various configurations described above, is also possible for such systems and from a manufacturing perspective would be simpler to accomplish than for a spiral-wound membrane module.

In some membrane modules, the membranes themselves are cylindrical in shape and electrodes may be readily placed in such modules on the two sides of these membranes.

In both the "Flat bed" and "Cylindrical" membrane modules all of the electrode configurations described previously may be incorporated in such module systems. Such electrodes would allow the monitoring of these membranes in the same manner as described for the Spiral-wound membrane module.

Another form of membrane module utilizes so call "Hollow fibre" membranes. These "hollow fibre" membranes consist of fine fibres, typically in the order of 1 mm in diameter which have a central void surrounded by material which itself is the membrane. A bundle of such hollow-fibres are usually incorporated in a complete module. The incorporation of electrodes on the outside the hollow fibre would be relatively easy to accomplish during manufacture. However, in many cases, it would be technically difficult to insert electrodes inside such hollow fibres without impeding the flow of fluid along its axis. The measurement of the membrane impedance as described above could still be performed once suitable electrodes are in place.

BRIEF DESCRIPTION OF THE DRAWINGS

Specific embodiments of the invention will now be described by way of example only and with reference to the accompanying drawings in which:

FIG. 10 schematically illustrates a method of measuring a system response in which a stimulus is applied only to a system under test;

FIG. 11 schematically illustrates a method of measuring a system response in which a stimulus is applied to both a reference system and a system under test;

FIG. 12 graphically illustrates a stimulus waveform and a response waveform to the stimulus for the system of FIG. 9.

DETAILED DESCRIPTION OF PREFERRED EMBODIMENTS

Figure 1:
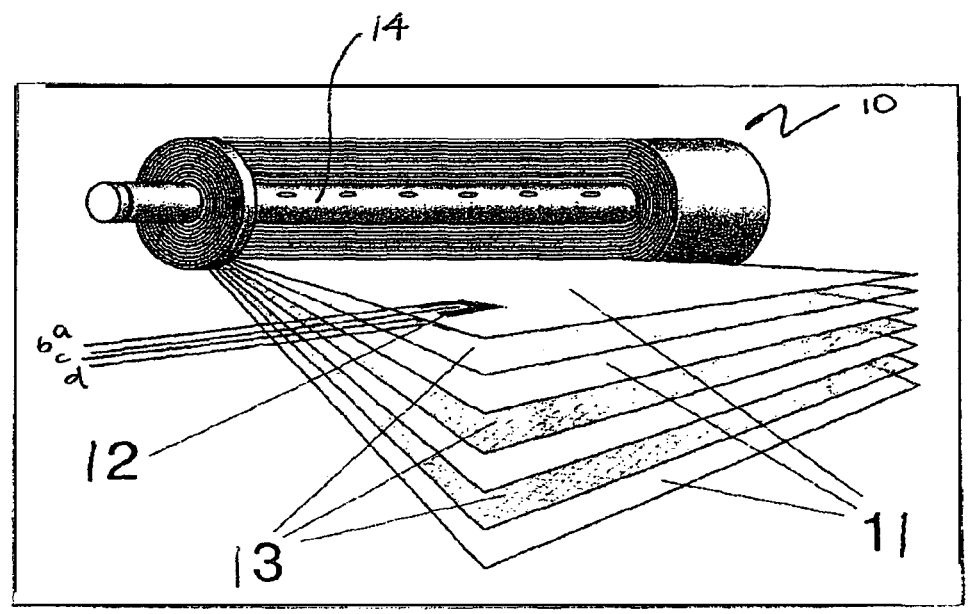
FIG. 1 shows a spiral-wound membrane separation module showing a cut-away view of the membranes.

Referring to the drawings, FIG. 1 shows a "spiral wound" membrane separation module 10 including electrodes 12. In the drawing part of the module is shown "unwound" showing a cut-away view of the membranes 11 and spacers 13, as well as the electrodes 12 located within the spacers.

In operation, feed fluid is driven under pressure on one side of each membrane 11 whilst the permeate is collected from the other side. The permeate moves radially towards the centre of the module 10 along the spacer 13 between adjacent membranes 11 to a central permeate collection tube 14. The feed fluid moves between adjacent membranes, longitudinally along the module. This also provides a so called "crossflow" that assists in preventing fouling of the membranes. The spacers 13 are usually constructed from about 1 mm thick polymer threads made into a fabric. The spacers 13 provide a space between adjacent membranes in both the feed side and permeate side.

FIG. 1 shows a system with two pairs of electrodes 12a, b, c, d located in the spacers 13 on the two sides of a single membrane 11. This electrode arrangement would be used with 4-terminal impedance measurements in which one pair 12a, b of electrodes on opposite sides of the membrane are used to inject the electric current stimulus signal and the other pair of electrodes 12c, d are used to measure the response signal. The impedance magnitude and phase are determined from the stimulus and response signals.

In use the two electrodes 12a, b on one side of a membrane in the module are used for injecting the stimulus signal and the further set of two electrodes 12c, d are used to measure the response signal developed across the membrane. The "four terminal method" of electrical impedance measurements is taught in International Patent Application No PCT/AU2007/000830 by Coster and Chilcott entitled "A System for complex impedance measurement". The manner in which these electrodes can be used to measure the impedance magnitude and phase is described in more detail below with reference to FIG. 4 and is further discussed with reference to FIGS. 9 to 12.

Figure 9:
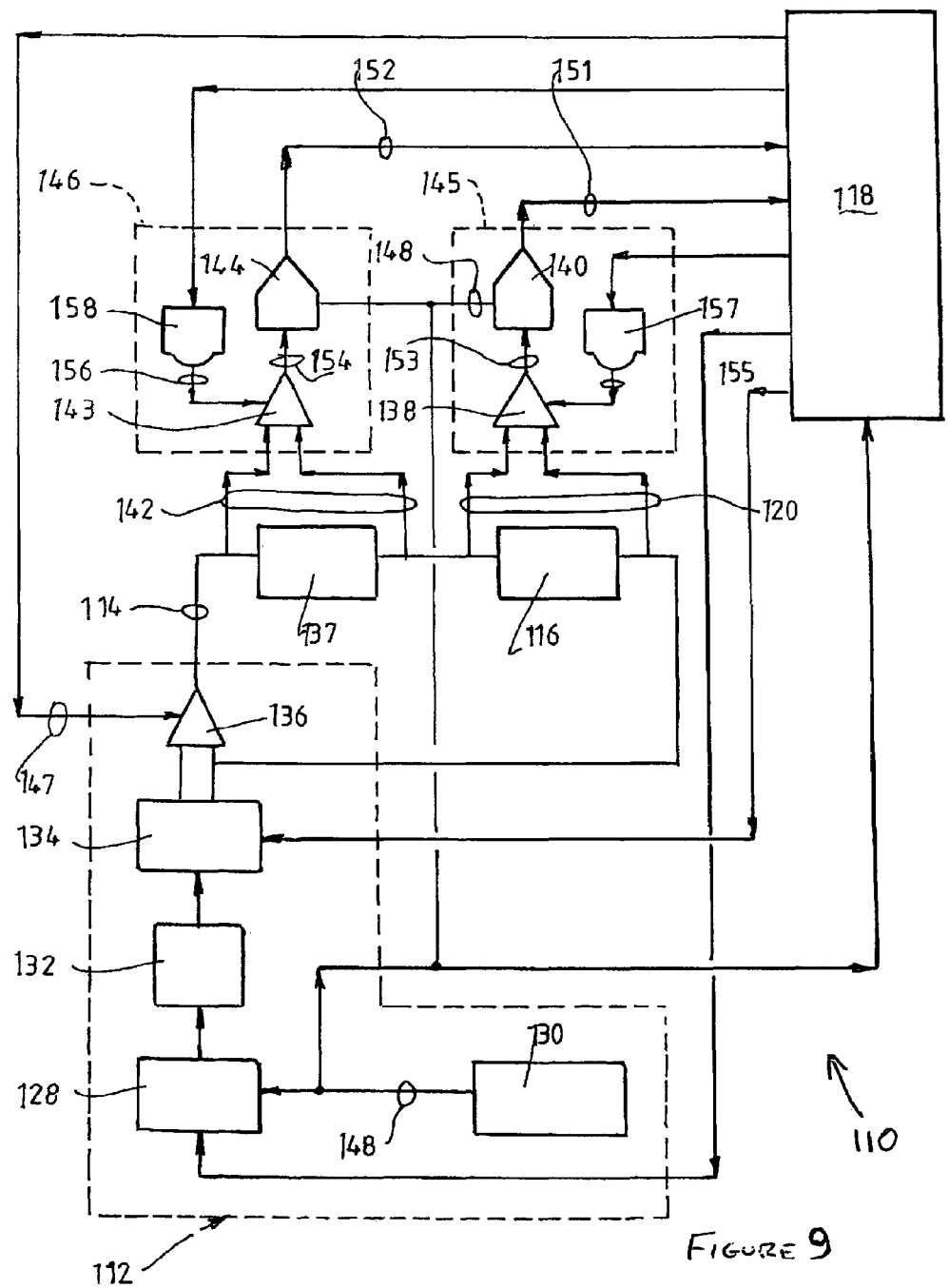
FIG. 9 shows a block diagram of a spectrometer in accordance with an embodiment of a measurement system for complex transfer function measurement.

With reference to FIG. 9 of the drawings, a system 110 for complex impedance measurement is illustrated schematically. The system 110 comprises a voltage signal source 112 for generating an input signal 114 to be applied to a system under test 116 and a reference system 137. The system 110 also includes a pair of detection circuits 145, 146 for detecting a response signal 120, of the system under test 116 and a response signal 142 of the reference system 137, in response to the input signal 114. The response signals 120, 142 typically include at least a response component 122 and a background component 124 (see FIG. 12). The system 110 further includes a processing system 118 which performs a signal analysis function that determines the gain and phase shift of the system 116 by comparing the response signal 120 to the input signal 114, and distinguishes the response component 122 from the background component 124 of the response signal 120. In the arrangement illustrated in FIG. 9 the reference system 137 and the system under test 116 are each two terminal systems and the characteristics of the system under test 116 are determined by comparing the ratio of the responses of the system under test 116 and the reference system 137 and using the known characteristics of the reference system to calculate the characteristics of the system under test.

The stimulus signal consists of an arbitrary waveform which is digitally defined and a full cycle of which is stored in an electronic memory 128 of the signal source 112. The arbitrary waveform may be a complex waveform defined by superimposing a plurality of periodic waveforms. Each periodic waveform may be a specific waveform, for example, sinusoidal, saw-tooth, triangle or square.

To read the arbitrary waveform from the electronic memory 128, a digital clock 130 is used to generate a pulsed clock signal 148 at a clock rate which determines the frequency range of the measurement. The clock rate determines the period T (see FIG. 12), and hence the frequency, of the arbitrary waveform 114. The digital read out of the arbitrary waveform is then converted to an analogue signal by a digital-to-analog converter (DAC) 132 and smoothed by filters 134. The analogue signal is then passed through an amplifier 136 in order to amplify the signal and produce the input signal 114 to be applied to the system under test 116 and the reference system 137. However, it is important that the amplifier 136 operates within its linear operating range, and to achieve this it has a gain control input to which a gain control signal 147 is supplied from the processor 118, as will be described in more detail below. The clock signal 148 is also provided to the processor 118 to enable synchronisation of the input and response signals during analysis.

As described above with reference to FIG. 8, the input signal 114 may be applied to a reference system 137, with known characteristics, as well as the system 116 under investigation as indicated in FIG. 10 or alternatively the input signal 114 may be applied only to the system 116 to be characterised as shown in FIG. 9. In the illustrated embodiment of FIGS. 9 & 12, the input signal is a voltage signal and the inputs of the test and reference systems are connected in series however it will be recognised that in some circumstances, depending upon the type of systems under test, an input may require to be driven by a current signal and/or the test and reference inputs may be connected in parallel.

The input signal 114 will cause the system under test 116 to produce a response signal 120 which in this case is a differential signal. Similarly the input signal 14 will cause the reference system 137 to produce a differential response signal 142. In order to measure the response signals 120, 142, the response signals 120, 142 are passed through output amplifiers 138, 143 and then digitally sampled by analogue-to-digital (ADC) converters 140, 144. The output offsets of output amplifiers 138, 143 are adjusted to avoid clipping by control signals 155, 156 provided from the processor 118 via D/A converters (DACs) 157, 158. For complex waveforms at least one full cycle of each of the digitised response signals 151, 152 are then passed to the processor 118 for storage and analysis. For pure sinusoidal waveforms it is possible to work with a smaller fraction of a complete cycle of the sine wave although it remains preferable to work with at least one complete cycle. The pulsed clock signal 148 of the clock 130, which is used to clock the arbitrary stimulus waveform from the electronic memory 128, are also used to clock the sampling of the amplified response signals 153, 154 so that the sampled response signals 151, 152 are synchronised with reading out from the digital waveform storage 128 of digital components used to create the input signal 114. Synchronising the generating of the input signal 114 and the sampling of the response signals 120, 142 reduces errors in measurement of the phase shift ($\Phi_R/\omega$), in particular, errors caused by erroneous zero-crossings as shown in FIG. 12.

Once the response signals 120, 142 have been sampled and stored within electronic memory in processor 118, the signal analysis function within processor 118 analyses the response of the system under test 16 and the reference system to determine and compare the respective transfer functions.

Referring again to FIG. 1, in the module 10, the electrodes 12 are electrically connected to electrode terminals on the outside of the pressure vessel (not shown) that encompasses the membrane module so that impedance measurements can be conducted without interruption of the operation of the module. The electrodes incorporated in the membrane module are constructed from a material that is a conductor of electricity, and the electrodes and the leads connecting to the electrodes should preferably be constructed out of the same conductive material to avoid complications that may arise from electrochemical reactions between different components when they are immersed in the fluids.

The leads connecting the electrodes to the outside of the module should preferentially be covered or coated with an electrically insulating material so that only the electrodes themselves are exposed.

The placement of the electrodes 12 within the module 10 can be designed to monitor various parts of the membranes within the module such as the feed side, discharge end and so on or the module may be fitted with multiple sets of electrodes to monitor the membrane at a variety of locations within the module.

Figure 2:
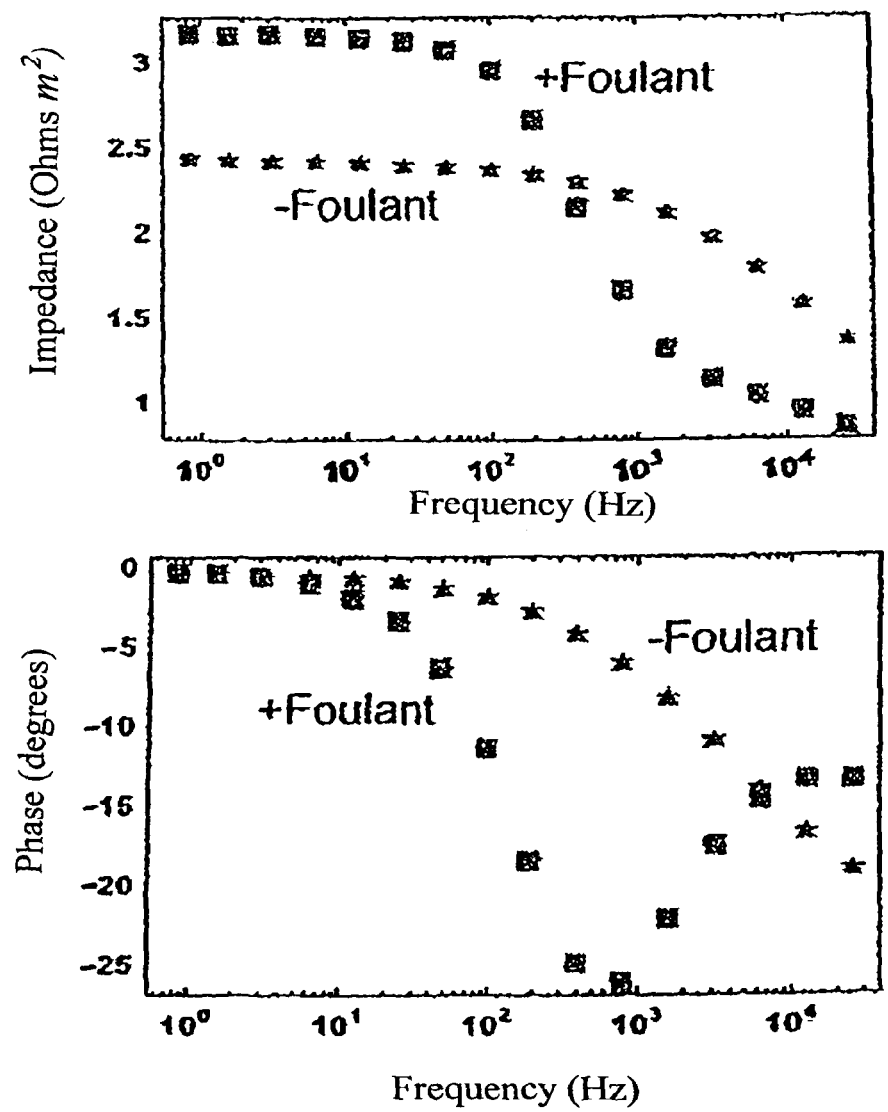
FIG. 2 shows graphs of impedance magnitude and impedance phase as a function of frequency with and without foulant.

FIG. 2 shows graphs of measured impedance magnitude and impedance phase as a function of frequency of a reverse osmosis membrane with and without foulant. The foulant in this case was calcium carbonate. The measurements were made with electrodes on the two sides of the membrane in a setup in which a small piece of the membrane was held in a flat-bed cell.

Figure 3:
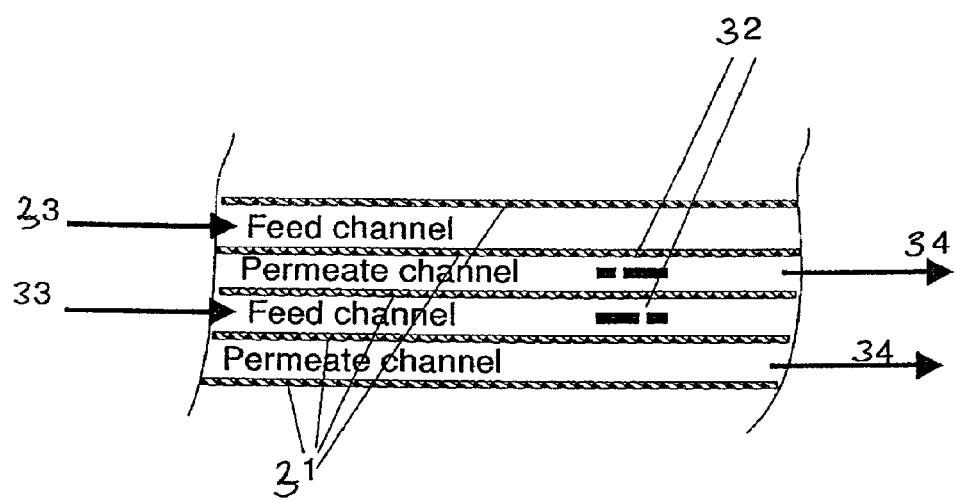
FIG. 3 is a schematic diagram illustrating four membranes separated by a fluid feed channel on one side and a permeate fluid channel on the other side.

FIG. 3 is a schematic diagram showing four membranes 31 separated by a feed fluid channel on one side 33 and a permeate fluid channel on the other side 34. Electrodes pairs 32 are shown located on two sides of a single membrane with one pair in a feed fluid channel and the other in a permeate fluid channel.

Figure 4:
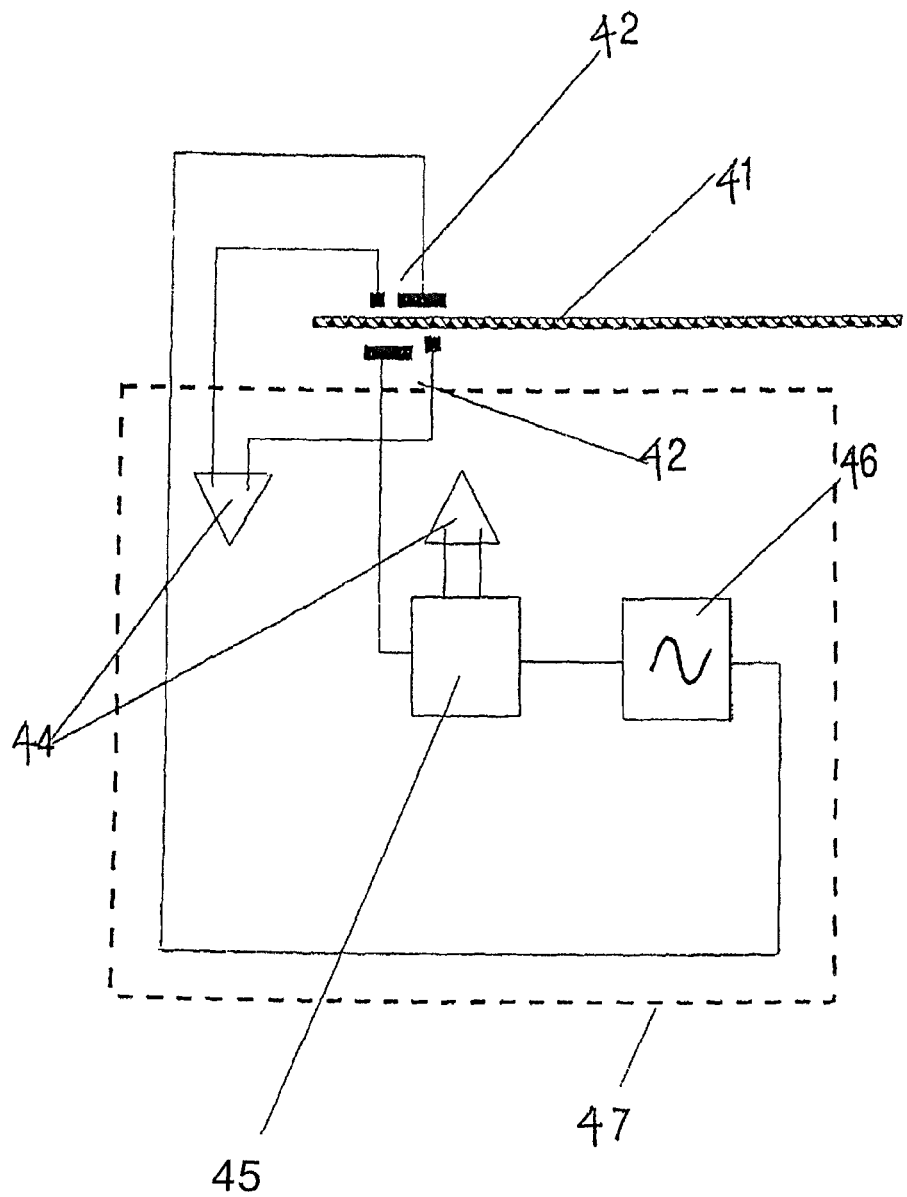
FIG. 4 is a schematic diagram illustrating two electrode pairs located on two sides of a membrane connected to an impedance spectrometer.

FIG. 4 shows two electrode pairs 42 that are located on the two sides of a membrane 41 connected to an impedance spectrometer 47 (indicated by the dotted box) designed for making four terminal measurements of impedance and phase. In such an instrument the AC current generated by a signal generator 46 is passed through a known or standard impedance element 45 and then via the electrodes 42 through the membrane. The response signal across the known impedance element and the response across the membrane is then measured using the signal amplifiers 44.

Figure 5:
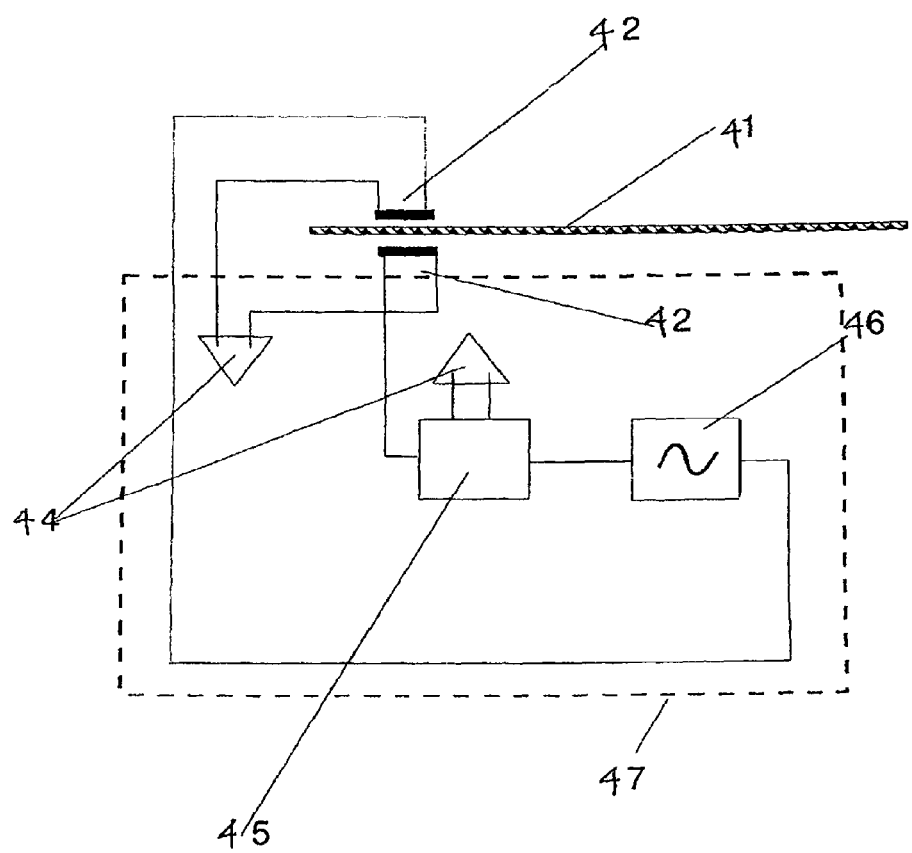
FIG. 5 is a schematic illustrating two single electrodes located on the two sides of a membrane connected to an impedance spectrometer.

FIG. 5 is similar to FIG. 4 except that it shows just two single electrodes 42 located on the two sides of a membrane 41, connected to the impedance spectrometer 47 to make two terminal measurements of impedance and phase. In such an instrument the AC current generated by the signal generator 46 is passed through the standard impedance element 45 and then via the electrodes 42 through the membrane. The response signal across the known impedance element and the response across the membrane is then measured using the signal amplifiers 44.

In this embodiment, in use, the impedance measurements can then be made using the same pair of electrodes to inject the stimulus signal and to measure the response.

Figure 6:
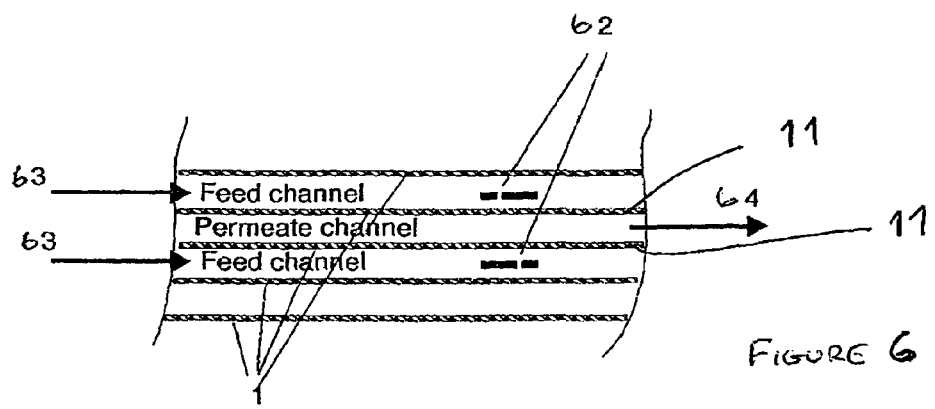
FIG. 6 illustrates the placement of two electrode pairs in two feed channels
Figure 7:
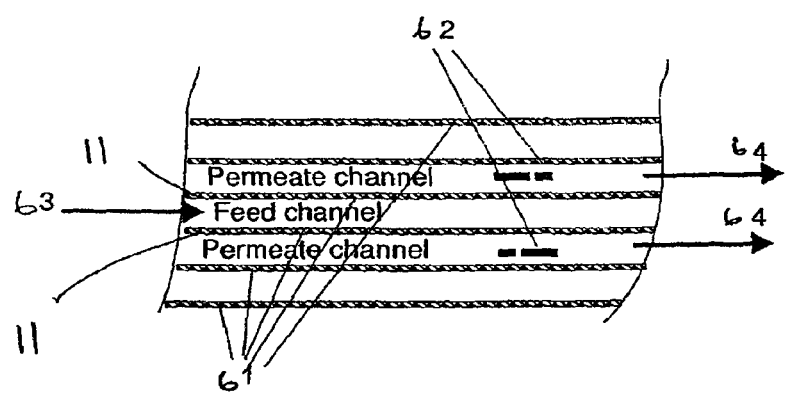
FIG. 7 illustrates the placement of two electrode pairs in two permeate fluid channels.

FIG. 6 illustrates the placement of two electrode pairs 62 such that the electrodes are in two feed fluid channels 63 and are separated by two membranes 11 and a permeate fluid channel. 64. FIG. 7 shows the placement of two electrode pairs 62 such that the electrodes are in two permeate fluid channels 64 and are separated by two membranes 11 and a feed fluid channel 63. In this way, in use, the stimulus signal is applied to two membranes 11 in series. This configuration can be used for four-terminal measurement, using four electrodes or a two terminal measurement using two electrodes (not illustrated).

There may be some advantage in making measurements in which both electrodes in the case of two-terminal measurements, or two pairs of electrodes in the case of four-terminal measurements, are present in the same solution, that is either in the feed solution or the permeate solution. This is because when such electrodes are in different solutions the electrochemical processes at the electrode-solution interfaces may create electric potential that produced voltage offsets. Whilst such voltage offsets can be allowed for in making the measurements, they may under severe circumstances reduce the precision that can be obtained in making the impedance magnitude and phase determinations.

The impedance measurements facilitated by the electrodes 62 placed in the membrane module, as described above in relation to FIGS. 6 and 7, may also be used in to monitor the electrical conductivity of the feed solution and or the permeate solution. Such information for the permeate fluid can provide an indication of loss of membrane integrity or important changes in the operational parameters such as a decrease in the, for instance, the salt rejection. Changes in the electrical conductivity of the feed solution may indicate important changes in the operational parameters that might require intervention. Whilst the configurations of electrodes described above in relation to FIGS. 6 and 7, where the electrodes or pairs of electrodes are separated by two membranes in series, would be particularly suited to making such measurements, the other configurations described above could also allow the fluid conductivities to deduced from the data.

Figure 8:
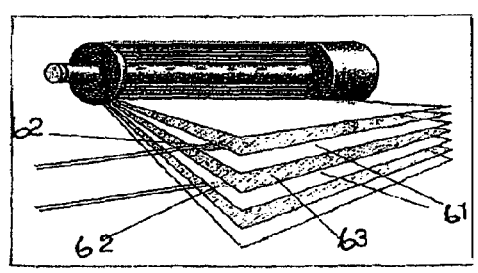
FIG. 8 illustrates the electrodes in a cut-away rolled out drawing of the membranes and spacers in a spiral wound module.

FIG. 8 illustrates the electrodes in a cut-away rolled out drawing of the membranes and spacers in a spiral wound module.

In one embodiment (not illustrated) the spacer fabric itself could be constructed out of an electrically conducting material such as stainless steel mesh and the spacer itself could then be used as the electrodes for the impedance measurements.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of in situ monitoring of a membrane separation system wherein the membrane separation system includes a separation membrane, and a pair of electrodes separated by the separation membrane, the method comprising:
using the membrane separation system to separate a feed solution into a permeate and a residue, where the permeate passes through the separation membrane and the residue remains on a feed side of the separation membrane;
applying an electrical alternating current stimulus through the separation membrane at one or more frequencies by applying the electrical stimulus between the pair of electrodes separated by the separation membrane;
measuring a response electrical potential between the pair of electrodes separated by the separation membrane;
comparing the electrical stimulus and the response electrical potential to determine a complex electrical impedance of the separation membrane at the one or more frequencies;
determining electrical conduction and electrical polarization properties of the separation membrane from the complex electrical impedance of the separation membrane at the one or more frequencies; and
monitoring changes of the electrical conduction and electrical polarization properties of the separation membrane indicative of changes in performance of the separation membrane.

2. The method of claim 1 wherein the electrical impedance measurements are made by passing the electrical alternating current stimulus through the separation membrane or a part of the separation membrane and measuring the response electrical potential as represented by a frequency dependant electrical response potential developed across the separation membrane and a phase difference between the stimulus current and frequency dependant response potential.

3. The method of claim 2 wherein fouling of the separation membrane is detected by monitoring the frequency dependant response potential for changes in the magnitude and relative phase of the frequency dependant response potential indicating a change in complex electrical impedance of the separation membrane.

4. The method of claim 1 wherein the pair of electrodes are located inside a membrane module comprising the separation membrane and the separation membrane comprises one or more separation membrane layers separated by a spacer fabric.

5. The method of claim 4 wherein the membrane module is fitted with electrodes located within the spacer fabric each on opposite sides of a separation membrane layer.

6. The method of claim 4 wherein the spacer fabric comprises an electrically conducting material, and two or more spacer fabrics are used as the pair of electrodes for performing the electrical impedance measurements, an electrode of the pair of electrodes is placed on each of a permeate side and a feed side of the separation membrane, the pair of electrodes used to inject the electrical stimulus currents and measure the response to the electrical stimulus extending over the entire length of the separation membrane and the pair of electrodes are located to apply the electrical stimulus signal and to monitor the electrical stimulus signal across two separation membranes in series, whereby the pair of electrodes are located in either two feed side channels separated by two separation membranes and a permeate channel or two permeate side channels separated by two separation membranes and a feed side channel.

7. The method as claimed in claim 4 wherein electrical impedance measurements facilitated by the pair of electrodes placed in the membrane module, are also used to monitor the electrical conductivity of the feed solution and or the permeate solution.

8. A membrane based separation device for removing or reducing the concentration of materials carried in a fluid comprising a separation membrane, a pair of electrodes, separated by the separation membrane, whereby an electrode of the pair of electrodes is placed on each of a permeate side and a feed side of the separation membrane, the pair of electrodes arranged to inject an electrical alternating current stimulus current at one or more frequencies and to make measurements across the separation membrane, for measurement of a complex electrical impedance of the separation membrane at the one or more frequencies to provide an indication of the electrical conduction and electrical polarization properties of the separation membrane.

9. The separation device of claim 8 comprising a membrane module, the pair of electrodes being located inside the separation membrane module.

10. The separation device as claimed in claim 9 wherein the separation membrane module is a flat sheet membrane module.

11. The separation device as claimed in claim 9 wherein the separation membrane module comprises hollow fibre separation membranes.

12. The separation device of claim 9 wherein the membrane module comprises one or more separation membrane layers separated by a spacer fabric.

13. The separation device of claim 9 wherein the membrane module is fitted with electrodes located within the spacer fabric each on opposite sides of a separation membrane layer.

14. The separation device of claim 12 wherein the spacer fabric comprises an electrically conducting material, and one or more of spacer fabrics are used as the electrodes for performing the electrical impedance measurements, one electrode of the pair of electrodes is placed on each of a permeate side and a feed side of the separation membrane, and the pair of electrodes extends over an entire length of the separation membrane.

15. The separation device of claim 12 wherein the spacer fabric is constructed of stainless steel mesh.

16. The separation device as claimed in claim 12 wherein the pair of electrodes are located to apply the electrical stimulus signal across two separation membrane layers in series, whereby the electrodes are each located in either two feed side channels separated by two separation membranes and a permeate channel or two permeate side channels separated by two separation membranes and a feed side channel.

17. The separation device as claimed in claim 12 wherein the membrane module comprises a spiral wound structure having a one or more of separation membrane layers separated by the spacer fabric.

\* \* \* \* \*